US009179237B2

(12) United States Patent
Pan et al.

(10) Patent No.: US 9,179,237 B2
(45) Date of Patent: Nov. 3, 2015

(54) VIRTUAL AUDIO SYSTEM TUNING

(75) Inventors: Davis Y. Pan, Arlington, MA (US); William M. Rabinowitz, Bedford, MA (US); Wontak Kim, Cambridge, MA (US); Hal Greenberger, Natick, MA (US)

(73) Assignee: Bose Corporation, Framingham, MA (US)

( * ) Notice: Subject to any disclaimer, the term of this patent is extended or adjusted under 35 U.S.C. 154(b) by 824 days.

(21) Appl. No.: 13/328,296

(22) Filed: Dec. 16, 2011

(65) Prior Publication Data

US 2013/0156213 A1 Jun. 20, 2013

(51) Int. Cl.
*G10K 11/16* (2006.01)
*H03B 29/00* (2006.01)
*A61F 11/06* (2006.01)
(Continued)

(52) U.S. Cl.
CPC .............. *H04S 7/00* (2013.01); *G10K 11/1788* (2013.01); *H04R 29/00* (2013.01); *G10K 2210/1082* (2013.01); *G10K 2210/1282* (2013.01); *G10K 2210/3046* (2013.01);
(Continued)

(58) Field of Classification Search
CPC .................. G10K 11/1788; G10K 2210/1282; G10K 2210/3046; G10K 2210/3055; G10K 2210/1082; G10K 2210/3048; H04R 2499/13; H04R 2420/01; H04R 29/00; H04S 7/00
USPC ............. 381/71.4, 71.1, 56, 58, 86, 302, 389
See application file for complete search history.

(56) References Cited

U.S. PATENT DOCUMENTS 5,434,922 A 7/1995 Miller et al.
6,829,361 B2 12/2004 Aarts
(Continued)

FOREIGN PATENT DOCUMENTS

EP 2026326 A1 2/2009
JP H02226999 A 9/1990
(Continued)

OTHER PUBLICATIONS

Olive, S.E., et al; Listener Loudspeaker Preference Ratings Obtained in situ Match Those Obtained via a Binaural Room Scanning Measurement and Playback System; (con't).
(Continued)

*Primary Examiner* — Paul S Kim
(74) *Attorney, Agent, or Firm* — Brian M. Dingman; Dingman, McInnes & McLane, LLP

(57) ABSTRACT

A method of virtually tuning an audio system that incorporates an acoustic compensation system, where the audio system is adapted to play audio signals in a listening environment over one or more sound transducers. The acoustic compensation system has an audio sensor located at a sensor location in the listening environment. The transfer functions from each sound transducer to the audio sensor location are inherent. The method contemplates recording noise at the sensor location, and creating virtual transfer functions from each sound transducer to the sensor location based on the inherent transfer functions from each sound transducer to the sensor location. Audio signals are processed through the virtual sound transducer to sensor location transfer functions. A virtual sensor signal is created by combining the audio signals processed through the virtual sound transducer to sensor location transfer functions with the noise recorded at the sensor location.

25 Claims, 3 Drawing Sheets

(51) Int. Cl.
*H04S 7/00* (2006.01)
*G10K 11/178* (2006.01)
*H04R 29/00* (2006.01)

(52) U.S. Cl.
CPC ................. *G10K 2210/3048* (2013.01); *G10K 2210/3055* (2013.01); *H04R 2420/01* (2013.01); *H04R 2499/13* (2013.01)

(56) References Cited

U.S. PATENT DOCUMENTS

| | | | | |
|---|---|---|---|---|
| 8,175,286 | B2 | 5/2012 | Bech et al. | |
| 2008/0212788 | A1* | 9/2008 | Bech et al. | 381/59 |

FOREIGN PATENT DOCUMENTS

| | | | |
|---|---|---|---|
| JP | H02300638 | A | 12/1990 |
| JP | H06141392 | A | 5/1994 |
| JP | H09230875 | A | 9/1997 |
| JP | 2005338453 | A | 12/2005 |
| JP | 2008546270 | A | 12/2008 |
| WO | 2006/126161 | A2 | 11/2006 |
| WO | 2011/112417 | A1 | 9/2011 |

OTHER PUBLICATIONS (con't) Audio Engineering Society Convention Paper 7034, May 5-8, 2007, Vienna Austria.

Hiekkanen, T., et al; Virtualized Listening Tests for Loudspeakers; Audio Engineering Society Convention Paper 7367, May 17-20, 2008, Amsterdam, The Netherlands.

Granier, E., et al; Experimental Auralization of Car Audio Installations; Journal of Audio Engineering Society; vol. 44, No. 10, Oct. 1996.

Binaural Audio in the Era of Virtual Reality; Journal of Audio Engineering Society, vol. 55, No. 11, Nov. 2003.

Christensen, F., et al; A Listening Test System for Automotive Audio—Part 1: System Description; Audio Engineering Society Convention Paper 6358; May 28-31, 2005, Barcelona Spain.

International Search Report and the Written Opinion of the International Searching Authority dated Mar. 5, 2013 for PCT/US2012/066740.

Office Action issued on Jul. 7, 2015 in the corresponding Japanese Application No. 2014-547261 with machine translation.

* cited by examiner

VIRTUAL AUDIO SYSTEM TUNING

FIELD

This disclosure relates to tuning of audio systems.

BACKGROUND

Audio systems can include the capability to change one or more parameters of the audio signals to cause a desired effect in the sound perceived by a listener in the listening environment. The effects caused are typically variation of the signal level and/or the equalization of the sound in the listening environment. Audio system designers developing systems for use in noisy environments, such as motor vehicle cabins, airports, restaurants, etc., desire to use the systems in the actual environment while retaining the capacity to tune the system's dynamic parameters, with the aim of developing a system that performs well under different conditions of the listening environment. This effort requires repeated and extensive use of the listening environment under actual use conditions, which can be difficult and expensive.

Some audio systems for listening environments in which noise in the listening environment can change are dynamically adjusted in an attempt to account for the changes in noise. One example of such an environment is the cabin of a motor vehicle. Engine sounds, road noise, and noise from other conditions of the listening environment such as wind noise associated with the state of the vehicle windows (up, partially open or fully open) affect the perception of sounds being played over the audio system. One acoustic compensation system senses the sound in a motor vehicle interior, extracts the noise from the sensed sound, and adjusts the audio signals in a predetermined manner to account for the noise. For example, the reproduction level, dynamic range, and frequency response can be varied based on an analysis of the noise.

It can also be desirable to alter the perception of engine sounds in a vehicle cabin, for example by canceling or enhancing them. Audio systems incorporating acoustic compensation systems can accomplish this by creating audio signals based on the engine harmonics.

Systems that allow virtual evaluation of certain aspects of audio systems are known. For example, virtual listening via headphones can be used for subjective evaluation. Such virtual listening systems can include the addition of pre-recorded noise to the audio output, to mimic the actual environment.

SUMMARY

In order for an audio system incorporating an acoustic compensation system to operate effectively, the audio system must be tuned; i.e., the values of the dynamic parameters need to be established based on actual use conditions. For vehicle audio systems, tuning requires that the vehicle be operated under varied vehicle operating conditions that mimic the conditions that are likely to be experienced by the user. This typically requires measurement of noise at one or more noise sensor locations in the vehicle interior as the vehicle is operated under varied conditions such as engine RPM, vehicle speed, road surface conditions, and the state of the vehicle windows. Proper tuning of the audio system incorporating the acoustic compensation system thus requires extended and substantial access to the particular listening environment, e.g., the vehicle.

By contrast to conventional approaches, certain embodiments of the present innovation contemplate recording sound at the one or more sensor locations in the listening environment and simultaneously monaurally or binaurally recording sound at one or more sound evaluation locations in the listening environment. It is desirable to calibrate the recording so that the recorded sounds can be played back at the same level at which they were present during the recording. Additional non-acoustic signals pertaining to the sound in the listening environment may also be recorded. Examples of such signals include engine RPM, throttle position, and/or engine torque associated with vehicle engine noise. The engine RPM signal defines the engine harmonic frequencies while the throttle position and/or engine torque help define the level of the engine noise for harmonic enhancement. The transfer functions from each loudspeaker to each acoustic sensor location and each sound evaluation location are virtualized. The acoustic sensor signals can then be virtualized and fed back to the acoustic compensation system controller. This allows the audio system to be tuned without the need to operate the vehicle during the tuning process. It is desirable to calibrate the measurement and virtualization of transfer functions, so that signals played back through the virtualization system are output with the proper level relative to the recorded noise levels. The result is that the tuning engineer can tune the system at any time or place once the vehicle has been operated under desired operating conditions for purposes of recording sound and non-acoustic signals at sensor and evaluation locations.

In some embodiments, the innovation comprises the application of virtualization to the tuning of an acoustic compensation system that works with an audio system to play back signals into a listening environment. The acoustic compensation system may alter operating parameters of the audio system, it may alter the signals reproduced by the audio system, or both. The acoustic compensation system is used to alter signals rendered by the audio system in the listening environment in some way dynamically, in response to variation in the operating conditions of the systems that affect the listening environment. The acoustic compensation system receives one or more inputs. At least some of the inputs are from sensors (acoustic or non acoustic) that have non-stationary statistics. That is, the sensor output signal statistics are time varying. In general, the sensor output signal statistics vary with the operating characteristics of the environment. In an embodiment adapted for use in a vehicle, the sensor output statistics vary with operating state of the vehicle (speed, transmission gear, state of vehicle windows, etc.). Acoustic sensors are virtualized. Non acoustic sensors and/or other system inputs that are not affected by output from the audio system (e.g., engine RPM) are recorded. A controller within the acoustic compensation system forms an output based on the received inputs. The controller may have a feedforward or feedback topology, or may exhibit characteristics of both. The controller may operate open or closed loop. The controller may be time invariant or adaptive. The output of the controller may alter operating parameters of the audio system, it may alter the signals reproduced by the audio system, or both.

In one example where the listening environment is a vehicle passenger cabin, the acoustic compensation system alters operating parameters of an audio system for rendering desired audio program information in the listening area (the cabin). The parameters are altered based on ambient noise present in the environment, to improve audibility of the rendered audio signals in the presence of noise. The parameters are altered dynamically in response to dynamic changes in the noise.

In another example where the listening environment is again a vehicle passenger cabin, the acoustic compensation system alters characteristics of a signal correlated with the vehicle engine signature and outputs this signal through the audio system. The dynamically varying output signal interferes with the engine signal present in the listening environment to alter the perception of the engine signature by a listener located in the listening environment (the vehicle cabin). In one instance, the altered signal interferes destructively with the engine noise, in another instance it interferes constructively. The altered signal may be a broadband replica of the engine noise signature, or it may be representative of one or more individual harmonics of the fundamental frequency of the engine signature. The signal may destructively interfere with some harmonics and constructively interfere with other harmonics.

The acoustic compensation system has one or more sensors located somewhere within the listening environment; at least some of these sensors are typically acoustic sensors such as microphones. The system may also have one or more non-acoustic sensors which sense parameters pertaining to the environmental noise and/or one or more non-acoustic inputs that pertain to noise, such as an engine RPM signal received from the automobile's engine control unit. The non-acoustic sensors or other non-acoustic inputs may include engine RPM, throttle position, or engine load, which pertain to vehicle engine noise. The system can use these inputs to determine how to alter the system or process signals to achieve some desirable state.

Virtualization of an audio system is known. It is possible to synthesize the interaction of an audio system with a listening environment, so that an individual can listen to signals that are representative of signals that would be present if that person were physically located in the listening environment listening to the real, physical audio system. The signals can be reproduced over headphones or loudspeakers. To date, such virtualized audio systems have been static; they have not been able to account for dynamically varying conditions. The virtualizations have only been done at evaluation locations. That is, only at the locations of a listener's ears.

An innovation herein is that use of an acoustic compensation system requires the use of sensors to sense some condition within the space that the system is trying to compensate. In order to virtually tune such a system, it is not sufficient to virtualize just an evaluation point; one must also record sensor signals or other system inputs that relate to the listening environment, or virtualize sensors used by the system. In addition to generating virtual signals representative of the signals present at the evaluation point, the virtualized acoustic compensation system also needs access to the sensor signals that would be present in the real environment. Only then can the virtual version of the acoustic compensation system output signals that would be representative of the real signals that would be output by the physical system exposed to the same environment. Virtualization of the sensor signals which can be affected by the acoustic compensation system is required.

Described herein are multiple manners of virtualizing the evaluation point. In the first example of a system used to alter the audio system parameters to improve audibility of desired signals rendered by the system in the presence of noise, it is desirable for the engineer tuning the system to listen to the audio system as if he were present in the real vehicle. This is best done by virtualizing binaural signals at the evaluation point, as is known for simple virtual listening to static (non time-varying) audio systems. In the second example where the character of engine sound is being altered by the acoustic compensation system, it is not necessary to use binaural virtualization at the evaluation point. Virtualization of the signal present at a single point in the vicinity of a listener's head is sufficient to determine if the engine sound has the correct character. It is even possible to determine this objectively for the case of EHC (engine harmonics cancellation), where an objective measure of desired reduction in SPL (sound pressure level) may be available. Although it is not necessary to use binaural virtualization for EHC and EHE (engine harmonics enhancement) applications, it is certainly possible to do so, and in some cases a tuning engineer may also want to listen to the modified engine sounds. Additionally, since EHC and EHE may be used simultaneously with the audio system, the tuning engineer may wish to listen to the virtual vehicle cabin system with both systems running simultaneously.

In general, one aspect of the disclosure features a method of virtually tuning an audio system that incorporates an acoustic compensation system, where the audio system is used to play audio signals over one or more sound transducers in a listening environment. The acoustic compensation system has a sensor located at a sensor location in the listening environment. The transfer functions from each sound transducer to the sensor location are measured and stored. The method contemplates recording noise at the sensor location. Virtual transfer functions from each sound transducer to the sensor location are created based on measured transfer functions from each sound transducer to the sensor location. Audio signals are then processed through the virtual sound transducer to sensor location transfer functions. A virtual sensor signal is created by combining the audio signals processed through all the virtual sound transducer to sensor location transfer functions with the noise recorded at the sensor location. This virtual sensor signal can then be used in the audio system tuning effort, or otherwise, as a real-world noise sensor output would be used in an actual audio system.

Various implementations may include one or more of the following features. There may be a sound evaluation location in the listening environment, and the transfer functions from each sound transducer to the evaluation location may be measured. The method may further comprise recording noise at the sound evaluation location simultaneously with recording noise at the sensor location, creating virtual transfer functions from each sound transducer to the evaluation location based on inherent transfer functions from each sound transducer to the evaluation location, processing audio signals through the virtual sound transducer to evaluation location transfer functions, and creating an audio evaluation signal by combining the audio signals processed through all the virtual sound transducer to evaluation location transfer functions with the noise recorded at the sound evaluation location.

The acoustic compensation system may further comprise a processor that processes the audio signals, and the method may further comprise inputting the virtual sensor signal to the processor, wherein the virtual sensor signal is used by the processor to cause modifications to the audio signals that are played as part of the audio evaluation signal (i.e., played in the virtualized listening environment). The method may still further comprise inputting to the processor one or more acoustic compensation system inputs selected from the group of inputs including an engine RPM signal, a music signal, a signal representative of vehicle speed, and a signal representative of the state of a vehicle function. These acoustic compensation system inputs may be used by the processor to cause modifications to the audio signals that are played in the virtualized listening environment.

The noise may be recorded binaurally, and the recorded noise may comprise sound in a vehicle cabin, where the sound may be recorded with the vehicle operating under particular, varied vehicle operating conditions. The method may further comprise associating (e.g., in a database) the recorded sound with the particular vehicle operating conditions at the times of the recordings. The method may still further comprise querying the database with particular vehicle operating conditions, to retrieve the sound recorded under such conditions, and creating the virtual sensor signal and the audio evaluation signal using such retrieved sound and recorded sound system inputs.

The acoustic compensation system may comprise multiple sensors located at multiple sensor locations in the listening environment, in which case the noise may be recorded simultaneously at all of the sensor locations. There may be multiple evaluation locations in the listening environment, and the noise may be recorded simultaneously at all of the sensor locations and all of the evaluation locations. The method may further comprise analyzing the audio evaluation signal, which may be accomplished by applying the audio evaluation signal to headphones. The sensor may be either a microphone or an accelerometer.

The recorded noise may comprise sound in the listening environment, and the sound may be recorded under varied environmental conditions of the listening environment. The method may further comprise associating in a database the recorded sound with the particular environmental conditions at the times of the recordings. The method may further comprise querying the database with particular environmental conditions, to retrieve the sound recorded under such conditions. The method may still further comprise creating the virtual sensor signal and the audio evaluation signal using the retrieved sound.

In general, in another aspect the disclosure features a method of virtually tuning an audio system with an acoustic compensation system, where the audio system is used to play audio signals over one or more sound transducers in a vehicle cabin. The acoustic compensation system comprises an adaptive processor that processes the audio signals, and a microphone located at a sensor location in the vehicle cabin. There is a sound evaluation location in the vehicle cabin. Transfer functions from each sound transducer to the sensor location are measured and stored, and transfer functions from each sound transducer to the evaluation location are measured and stored. The method comprises recording sound at the sensor location, and recording sound at the sound evaluation location simultaneously with recording sound at the sensor location, wherein the sound is recorded with the vehicle operating under particular, varied vehicle operating conditions. The recorded sound may be associated in a database with the particular vehicle operating conditions at the times of the recordings. Virtual transfer functions from each sound transducer to the sensor location are created based on the inherent transfer functions from each sound transducer to the sensor location. Virtual transfer functions from each sound transducer to the evaluation location are created based on the inherent transfer functions from each sound transducer to the evaluation location. Audio signals are processed through the virtual sound transducer to sensor location transfer functions, and audio signals are processed through the virtual sound transducer to evaluation location transfer functions. A virtual sensor signal is created by combining the audio signals processed through the virtual sound transducer to sensor location transfer functions with the sound recorded at the sensor location. An audio evaluation signal is created by combining the audio signals processed through the virtual sound transducer to evaluation location transfer functions with the sound recorded at the sound evaluation location. The virtual sensor signal is input to the processor; the virtual sensor signal is used by the processor to cause modifications to the audio signals that are to be played in the virtualized vehicle cabin. One or more acoustic compensation system inputs selected from the group of acoustic compensation system inputs including an engine RPM signal, a music signal, a signal representative of vehicle speed, and a signal representative of the state of a vehicle function are also input to the processor. These acoustic compensation system inputs are recorded simultaneously with the noise recordings at the sensor and evaluation locations. The acoustic compensation system inputs are used by the processor to cause modifications to the audio signals that are to be played in the virtualized vehicle cabin. The database may be queried with particular vehicle operating conditions to retrieve the sounds recorded under such conditions. The virtual sensor signal and the audio evaluation signal are then created using the retrieved sounds. The audio evaluation signal can then be analyzed, for example by applying the audio evaluation signal to headphones. The analysis can alternatively be accomplished objectively.

Various implementations of this aspect of the disclosure may include one or more of the following features. The acoustic compensation system may comprise multiple microphones located at multiple sensor locations in the vehicle cabin, and the sound may be recorded simultaneously at all of the sensor locations. There may be multiple evaluation locations in the vehicle cabin, and sound may be recorded simultaneously at all of the sensor locations and binaurally at all of the evaluation locations.

In general, in another aspect the disclosure features a method of virtually tuning an acoustic compensation system that is part of an audio system that is used to create audio signals that cancel or enhance engine harmonics in a vehicle cabin, the acoustic compensation system comprising a processor that processes the audio signals, and a microphone located at a sensor location in the vehicle cabin, wherein there is a sound evaluation location in the vehicle cabin, wherein transfer functions from each sound transducer to the sensor location are measured and stored, and wherein transfer functions from each sound transducer to the evaluation location are measured and stored. The method comprises simultaneously recording sound at the sensor location, recording sound at the sound evaluation location, and recording one or more engine-related signals. The sound recordings are made with the vehicle operating at various engine operating conditions. Virtual transfer functions from each sound transducer to the sensor location are created based on the inherent transfer functions from each sound transducer to the sensor location. Virtual transfer functions from each sound transducer to the evaluation location are created based on the inherent transfer functions from each sound transducer to the evaluation location. Audio signals are processed through the virtual sound transducer to sensor location transfer functions. Audio signals are processed through the virtual sound transducer to evaluation location transfer functions. A virtual sensor signal is created by combining the audio signals processed through the virtual sound transducer to sensor location transfer functions with the sound recorded at the sensor location. An audio evaluation signal is created by combining the audio signals processed through the virtual sound transducer to evaluation location transfer functions with the sound recorded at the sound evaluation location. The virtual sensor signal is inputted to the processor, wherein the virtual sensor signal is used by the processor to cause modifications to the audio signals that are to be played in the virtualized vehicle cabin, to cancel or enhance one or more engine harmonics. An engine RPM signal is also inputted to the processor. The engine RPM signal is recorded simultaneously with the recorded sounds, and is used by the processor to cause modifications to the audio signals played in the virtualized vehicle cabin. The virtual sensor signal and the audio evaluation signal are created using the retrieved sound. The audio evaluation signal is analyzed, which may be accomplished by applying the audio evaluation signal to headphones.

BRIEF DESCRIPTION OF THE FIGURES

The foregoing and other objects, features and advantages will be apparent from the following description of particular embodiments of the innovation, as illustrated in the accompanying drawings in which like reference characters refer to the same parts throughout the different views. The drawings are not necessarily to scale, emphasis instead being placed upon illustrating the principles of various embodiments of the innovation.

DETAILED DESCRIPTION

Embodiments of the present innovation contemplate recording sound at one or more sensor locations in the listening environment and simultaneously recording sound at one or more sound evaluation locations in the listening environment. Non-acoustic engine-related signals such as engine RPM, throttle position, engine load and/or engine torque can be recorded simultaneously with the sound recordings. Non-acoustic sensors can be used as necessary to sense such signals. Or, such signals may be provided by existing vehicle components or subsystems. Sound recording at the evaluation location(s) can be but is not necessarily binaural. The transfer functions from each loudspeaker to each sound sensor location and each sound evaluation location are virtualized. The sound sensor signals can then be virtualized and fed back to the controller of the acoustic compensation system. This allows the audio system that incorporates the acoustic compensation system to be tuned without the need to operate the vehicle during the tuning process. The result is that the tuning engineer can tune the system at any time or place once the vehicle has been operated under desired operating conditions for purposes of recording sound at the sensor and evaluation locations, and simultaneously recording non-sound signals.

Figure 1:
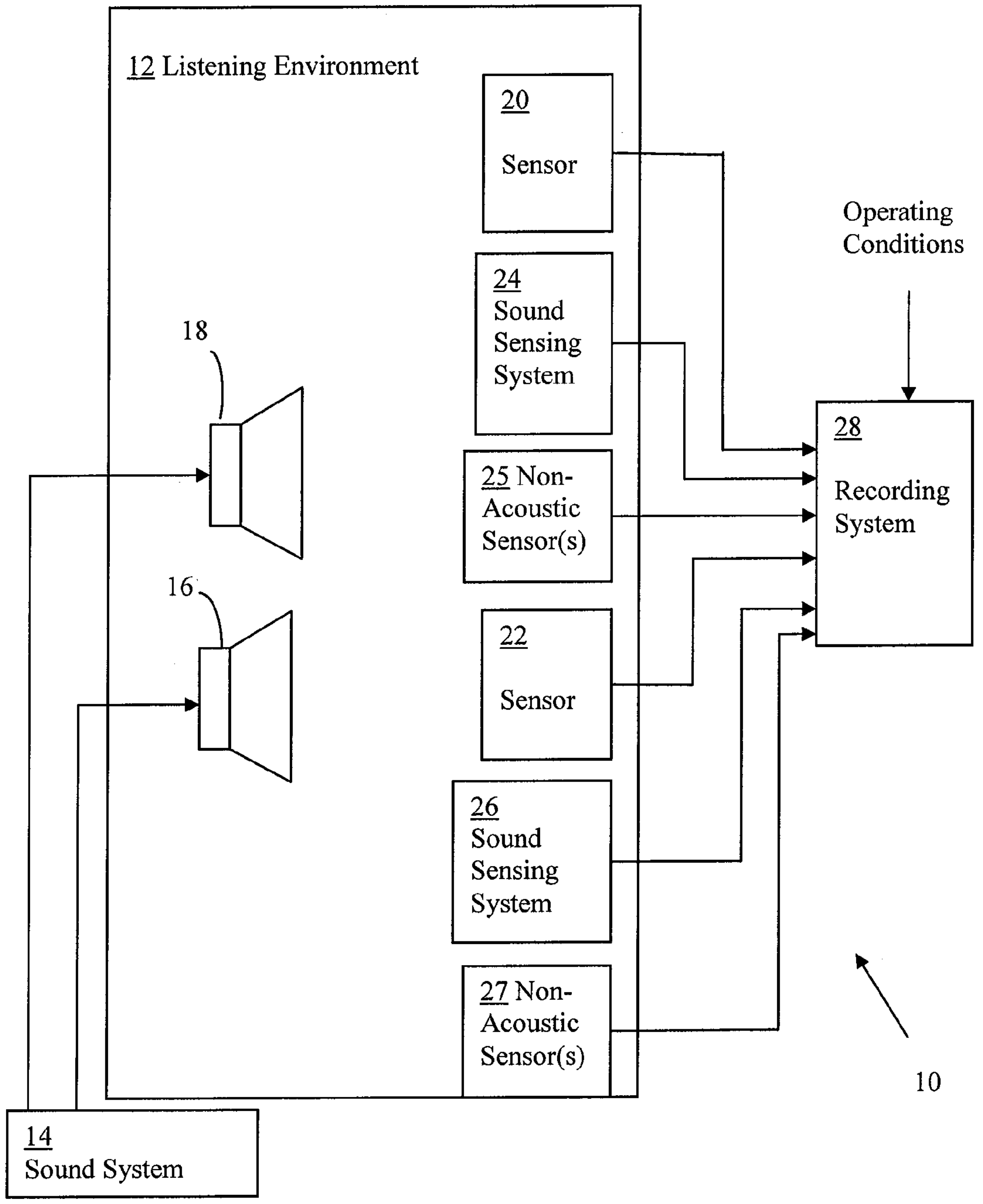
FIG. 1 is a schematic diagram of a listening environment which is used to record noise and/or non-acoustic signals, and which is adapted to employ a dynamic audio system of the type for which tuning can be simulated in accordance with the innovation.

Recording and sound system 10, FIG. 1, illustrates listening environment 12. Listening environment 12 is adapted to employ audio system 14 that plays audio in listening environment 12 over one or more loudspeakers, such as loudspeakers 16 and 18. The innovation herein allows for tuning of an acoustic compensation system that can be part of audio system 14.

Listening environment 12 can be a closed, partially closed or open environment. One example of a closed listening environment is the cabin of a motor vehicle. A partially closed listening environment can be a room or other interior venue with openings such as doorways, examples including public spaces such as restaurants. An open listening environment can be an outdoor venue in which music or other audio is to be played, or a large open indoor space or venue such as an airport concourse.

It is desirable to use virtual listening techniques to tune an audio system that includes an acoustic compensation system. One aspect of acoustic compensation system performance that requires tuning is the use of such systems for vehicle noise compensation. One type of vehicle noise compensation system contemplated herein is disclosed in U.S. Pat. No. 5,434,922, the disclosure of which is incorporated herein by reference. In this system, the loudness and/or equalization of audio played in a vehicle cabin is modified to compensate for the noise in the cabin. Another use of acoustic compensation systems in vehicles is for EHC/EHE, where engine sounds in the vehicle cabin are cancelled or enhanced. Such systems also need to be tuned.

In order for an acoustic compensation system to be tuned such that it operates appropriately, the system is operated under all relevant operating conditions and operational parameters of the listening environment; an audio engineer typically listens to the audio system output while present in the listening environment as the listening environment is subjected to the various conditions for which the system is to be tuned. At least some of these conditions are typically time varying. The engineer can modify acoustic compensation system parameters to achieve optimal audio results. Tuning thus requires both substantial access to the listening environment, and the tuning engineer's presence in the listening environment.

It is possible to synthesize the interaction of an audio system with a listening environment, so that an individual can listen to signals that are representative of signals that would be present if that person were physically located in the listening environment listening to the real, physical audio system. The signals can be reproduced over headphones or loudspeakers. To date, such virtualized audio systems have been static; they have not been able to account for dynamically varying conditions. The virtualizations have only been done at evaluation locations. That is, only at the locations of a listener's ears. For example, audio system performance in the presence of noise has been virtualized by recording noise in the actual listening environment ahead of time, and then mixing the recorded noise with the audio system output and playing the mixed signal to the tuning engineer over headphones. Such a system is disclosed in U.S. Patent Publication No. US2008/0212788A1, the disclosure of which is incorporated herein by reference.

Acoustic compensation systems can use one or more sensors to sense a time-varying condition that is in or will reach the space that the system is meant to compensate. An example of such a space is a listening environment such as a vehicle cabin. Sensors can include microphones for sensing sound, or vibration sensors such as accelerometers for sensing vibrations. In order to virtually tune such a system, both the evaluation location(s) and the sensor output(s) must be virtualized. Thus, in order to allow an acoustic compensation system to be tuned remotely from the listening environment (termed "virtual tuning" herein), the acoustic signal present at each sensor location must be recorded simultaneously with the recording of noise at the location or locations in the listening environment at which evaluation for the purpose of tuning would take place, termed herein the "evaluation location." Time-varying engine-related signals such as RPM, throttle position, and/or engine torque may be recorded simultaneously to the sound signal recordings.

FIG. 1 discloses a system that accomplishes simultaneous recording of noise and engine-related signals in listening environment 12 at one or more sensor locations and one or more sound evaluation locations. Sound sensor 20, which is typically a microphone, is located in environment 12 at a first sensing location (e.g., at what would be the location of one ear of a listener). Sound sensing system 24 is located in environment 12 at a first sound evaluation location. Engine-related non-audio signals can be sensed by non-acoustic sensor(s) 25; such sensors being located either in the listening environment or elsewhere. If the engine-related signals (e.g., RPM, throttle position, transmission setting) are already present in the vehicle they do not need to be sensed with a separate sensor but instead can be input directly from the vehicle to the acoustic compensation system. Regarding RPM, in some cases an analog RPM pulse can be taken from the engine control unit and the acoustic compensation system can derive the RPM based on the timing of the pulses. In other cases the engine control unit provides a digital signal representing the RPM value; this signal can be used directly by the acoustic compensation system. Second sound sensor 22 is located at a second sensor location (e.g., at what would be the location of the second ear of a listener), second sound sensing system 26 is located at a second sound evaluation location, and second non-acoustic sensor(s) 27 are located in the listening environment, or elsewhere.

Two sets of sensors are shown in FIG. 1 but that is not a limitation of the present innovation, which encompasses the use of at least one sensor, including zero or more acoustic sensors and zero or more non-acoustic sensors. Certain embodiments of this innovation contemplate one or more sound sensors at one or more sound sensor locations, and also contemplate one or more sound evaluation locations, all located in a particular listening environment. However, the innovation is not limited to any particular type of listening environment. For example, for virtual evaluation of an audio system for a vehicle cabin, one may wish to evaluate the sound in different seats. The vehicle cabin is asymmetric, and imbalances can arise. System engineers currently evaluate systems by listening in various seats. In EHE and EHC systems, how the signals from the audio system interact with the engine noise can vary from seat to seat. Multiple seats may be evaluated to make sure all positions within the vehicle are meeting a desired performance objective.

The outputs of all of the acoustic and non-acoustic sensors, and the outputs of the sound sensing systems, are provided to recording system 28. Also input to recording system 28 can be the material operating conditions/environmental conditions for the particular listening environment. For example, in vehicle noise compensation systems it is desirable to associate the operating conditions of the motor vehicle with the sensed sounds and the sensed non-acoustic signals. Parameters of operation of a motor vehicle that may be input to recording system 28 include an engine RPM signal, a signal representative of vehicle speed, and a signal representative of the state of another vehicle function. One vehicle function includes the state of each of the vehicle windows, whether closed, fully open, or partially open. For EHC/EHE systems, the engine RPM is the operating parameter of concern that can be associated with and recorded simultaneously with the recorded noise signals. When used, recording system 28 can associate the particular operating conditions with the sensor signals and sound recorded under such conditions.

The sound sensors are located in the listening environment, and detect sound at the sensors' locations. When microphones are used, the sensed sound is a combination of desired sounds (the audio system output) and noise present at the sensor location. The sensor output is fed back to the acoustic compensation system where the desired audio is removed from the signal to create a noise estimate representative of noise, typically via an adaptive process such as an adaptive noise canceller as is known in the art. This noise estimate is used by a controller of the acoustic compensation system to generate control signals for the audio system that result in the desired audio system output changes designed to compensate for the noise present in the environment. For example, the volume and/or equalization of the audio can be modified so that the audio remains audible over the noise.

Another example of a sensor is a vibration sensor. Vibration signals can be used if they are correlated with the noise that is being compensated for or altered. For example, an accelerometer on the vehicle engine may have a signature correlated with the acoustic signature present in the vehicle cabin. One could mount accelerometers to other noise sources, such as the transmission housing. An accelerometer mounted to a wheel suspension strut may provide a signal representative of road noise in the vehicle cabin. The higher the correlation of the sensor signal with the ambient noise in the environment, the more useful the non-acoustic sensor can be. An accelerometer output signal also is likely much less sensitive to output from the audio system than a microphone. When trying to form an estimate of the noise present in the vehicle cabin, a vibration signal may be more useful than a microphone signal, as long as the vibration signal is well correlated with the acoustic noise, because the vibration signal is not corrupted by the audio system output.

Figure 2:
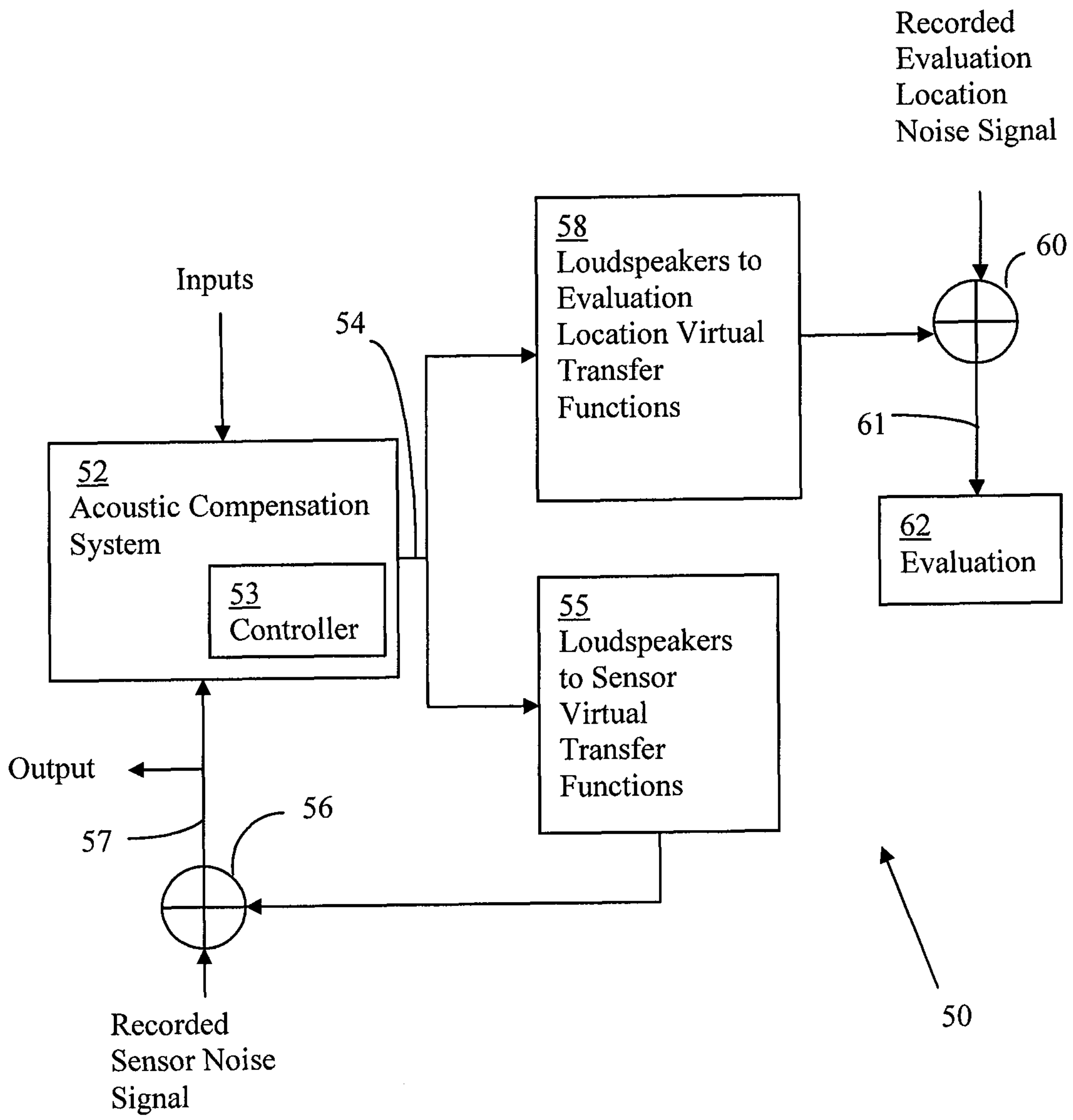
FIG. 2 is a schematic diagram of a system for use in simulated tuning of a dynamic audio system.

System 50, FIG. 2, can be used to accomplish virtual evaluation of an audio system that includes an acoustic compensation system, e.g., for virtual tuning purposes. Virtual evaluation 62 is accomplished in one example by creating a virtual audio signal 61 that is played to a person, such as the tuning engineer, over headphones or loudspeakers. The virtual audio signal is a signal that is analogous to the sound that a person located at the relevant evaluation location would hear with the audio system operating under the relevant operating conditions. For a vehicle noise compensation system, the evaluation location would be a location in the vehicle cabin. The selected operating conditions could include one or more of the conditions set forth above, such as engine RPM, vehicle speed, road surface conditions, and window state. The virtual audio signal 61 would comprise a combination of audio signals modified by acoustic compensation system 52 to account for the noise, and the noise recorded at the relevant evaluation location(s) under the particular selected vehicle operating conditions. For a vehicle EHC/EHE system, the virtual audio signal 61 could comprise a combination of audio signals modified by system 52 to cancel or enhance the engine harmonics, and the noise recorded at the relevant evaluation location at the relevant engine RPM.

In virtual evaluation system 50, transfer functions from each of the loudspeakers to each of the sensor and evaluation locations must be predetermined and stored in the system. Determining transfer functions from loudspeakers to sensors and/or to the ear(s) of a listener (i.e., the evaluation locations) is known in the art. For example, a filter can be synthesized that has a transfer function that matches the measured transfer function from one source to one position (sensor or evaluation position). Such filters can be synthesized for each loudspeaker to each sensor and each evaluation location. For example, the left front speaker to microphone sensor transfer function may be measured. A filter is then synthesized that has the same impulse response as the measured transfer function (as closely as practical, as is known in the art). The signal that feeds the left front speaker is then convolved with the filter impulse response to form an output signal that would be representative of the actual signal present at the microphone due to the input signal to the left front speaker being played by the left front speaker into the listening environment. Such transfer functions, and the manner in which they are used in accordance with the innovation herein, are termed "virtual transfer functions."

In system 50, a virtual sensor output signal 57 comprises the combination 56 of recorded noise at an acoustic sensor, and audio signal 54 output by acoustic compensation system 52 that has been processed through the loudspeakers to sensor virtual transfer functions 55. Signal 57 thus is analogous to the output of a real-world microphone located at the sensor location in the listening environment at which the noise was recorded. System 52 can use signal 57 as an input in a manner appropriate for the adaptations to the audio signals that are responsive to such an input. System 52 preferably includes a controller 53. System 52 may be adaptive or not. Inputs to system 52 can include parameters that are capable of causing system 52 to modify the audio signals.

There are at least two manners in which system 50 can be used for virtual tuning. One manner of use is subjective evaluation 62—allowing a person to tune an audio system without the need for the person accomplishing the tuning to be present in the listening environment, or for the environment to be operated in its normal fashion during the tuning procedure (e.g., while the motor vehicle is running). This is provided for via audio evaluation signal 61 that is a combination 60 of the noise signal recorded at the particular evaluation location(s) and the audio signal 54 processed through the loudspeakers to evaluation location(s) virtual transfer functions 58. Signal 61, in this case, is binaural and thus accounts for two evaluation locations (two ears), and is typically provided to a set of headphones that are worn by a tuning engineer. Signal 61 emulates the sound that would be heard if the person was sitting in the vehicle with his ears at the evaluation locations hearing the audio signal 54 in combination with the noise in the vehicle cabin existing under the selected vehicle operating conditions, the noise in this case having been previously recorded. Evaluation signals provided to headphones are typically a binaural pair of signals, one signal for each ear. Each ear signal is formed from the recorded binaural signal and the virtual transfer function associated with that ear location; each ear has its own virtual transfer function.

As an alternative to such subjective evaluation, an objective evaluation 62 can be performed. An objective evaluation can be accomplished by iteratively modifying each of the tuning parameters for the particular audio system. Evaluation 62 would then make an objective determination or measurement of the resulting changes in signal 61. For example, for a vehicle noise compensation system the result can be the sound level in the virtual cabin at various frequencies or frequency bands. As another example, for objective evaluation of a vehicle EHC or EHE system, the objective evaluation can determine the sound spectrum in relation to the changed audio system parameters to determine the parameter settings that accomplish the maximum performance of the EHC/EHE system, as such desired performance has been predefined. For example, in a case in which one or more engine harmonics in the vehicle cabin are to be cancelled or reduced by such a system, the objective measurement would be the SPL at the frequency or frequencies of interest. As another example, for an EHE system that is designed to augment engine harmonics in a particular manner, the objective system would measure the SPL at the relevant frequencies and compare the measurements to the desired outcome.

Engine noise has a fundamental (i.e., lowest frequency component) that is associated with engine RPM. The signature of the engine is primarily made up of this fundamental, plus a number of higher order harmonic components. A harmonic is a frequency related to the fundamental by a usually integer multiple. Half multiple harmonics are also possible. EHC and EHE systems select some finite number of harmonics (and possibly the fundamental) to alter in some manner (either increase or decrease in magnitude). The end goal is determined subjectively. The virtual tuning herein provides the ability to vary harmonics in a manner designed to reach the desired endpoint. The complete signature of the engine is determined by the magnitude and phase of all harmonics, where phase means the phase relationship relative to a reference harmonic. Acoustic compensation system 52 alters the signature by altering the magnitude and/or phase of some number of harmonics. Objective criteria can be developed a priori, and the system can be evaluated virtually so as to obtain this objective measure. Properties of system 52 are altered to best achieve the desired end state.

An EHC or EHE system uses an engine RPM signal to determine the frequency of the engine harmonic. The engine RPM signal can be recorded along with the noise, and can be an input to system 52. Other inputs can be throttle position or engine load, for example. The EHC or EHE system can be preconfigured to either cancel the harmonic, or enhance it or change it in some other way to achieve a desired engine sound in the vehicle cabin. The EHC or EHE system generates sound at appropriate frequencies and magnitudes. The sound is played over the cabin loudspeakers to accomplish the desired result. System 52 adjusts the magnitude and phase of the sound to achieve the desired result. In the case of cancellation, the magnitude and phase is adjusted to minimize the level of sound at the frequency of interest at the in-cabin sensor (microphone), which ideally is at or very close to the evaluation location. The sound sensed by the sensor is the acoustic sum of the noise at this frequency (which is typically exclusively or primarily noise produced by the engine at this frequency) together with the sound produced by the EHC loudspeakers. The EHC microphone sensor signal is thus the error signal that is minimized by the EHC system in the case of cancellation. For EHE, system 52 alters the sound to accomplish a desired harmonic signature. In an EHE system there may be no sensors and no feedback; engine signals such as RPM, throttle position and engine torque can be inputs to system 52, which then determines and outputs appropriate audio signals that accomplish desired engine harmonic enhancement. Evaluation for an EHC or EHE system can be at a single point, or can be binaural.

In the present innovation, the vehicle and either the test track or the dynamometer on which the vehicle is run needs to be accessed only once, for recording of noise measurements. For EHC or EHE systems, non-acoustic signals such as engine RPM can be recorded. System 50 typically uses as one input to system 52 the engine RPM. The predetermined virtual transfer functions replace the acoustic paths that exist in the real world from the loudspeakers to the audio sensor and evaluation microphones. Signals 57 and 61 will thus closely match real-world performance. In the case of EHC, the amount of noise cancellation can be objectively determined. Thus the evaluation 62 accomplished by iterative tuning of the relevant system parameters can be automated. This can be accomplished with an optimizing program which iteratively modifies each EHC tuning parameter, one at a time, to determine the tuning which maximizes EHC performance at the measurement microphones (i.e., at the evaluation location(s)).

In some examples of acoustic compensation systems, the virtual sensor signal 57 is not fed back to system 52. In such cases signal 57 can be considered the output of the system. In an EHC system, signal 57 is fed back to an adaptive system 52. An EHE system may not use an audio sensor, in which case signal 57 does not exist; the output of block 58 is then the output of system 50.

Figure 3:
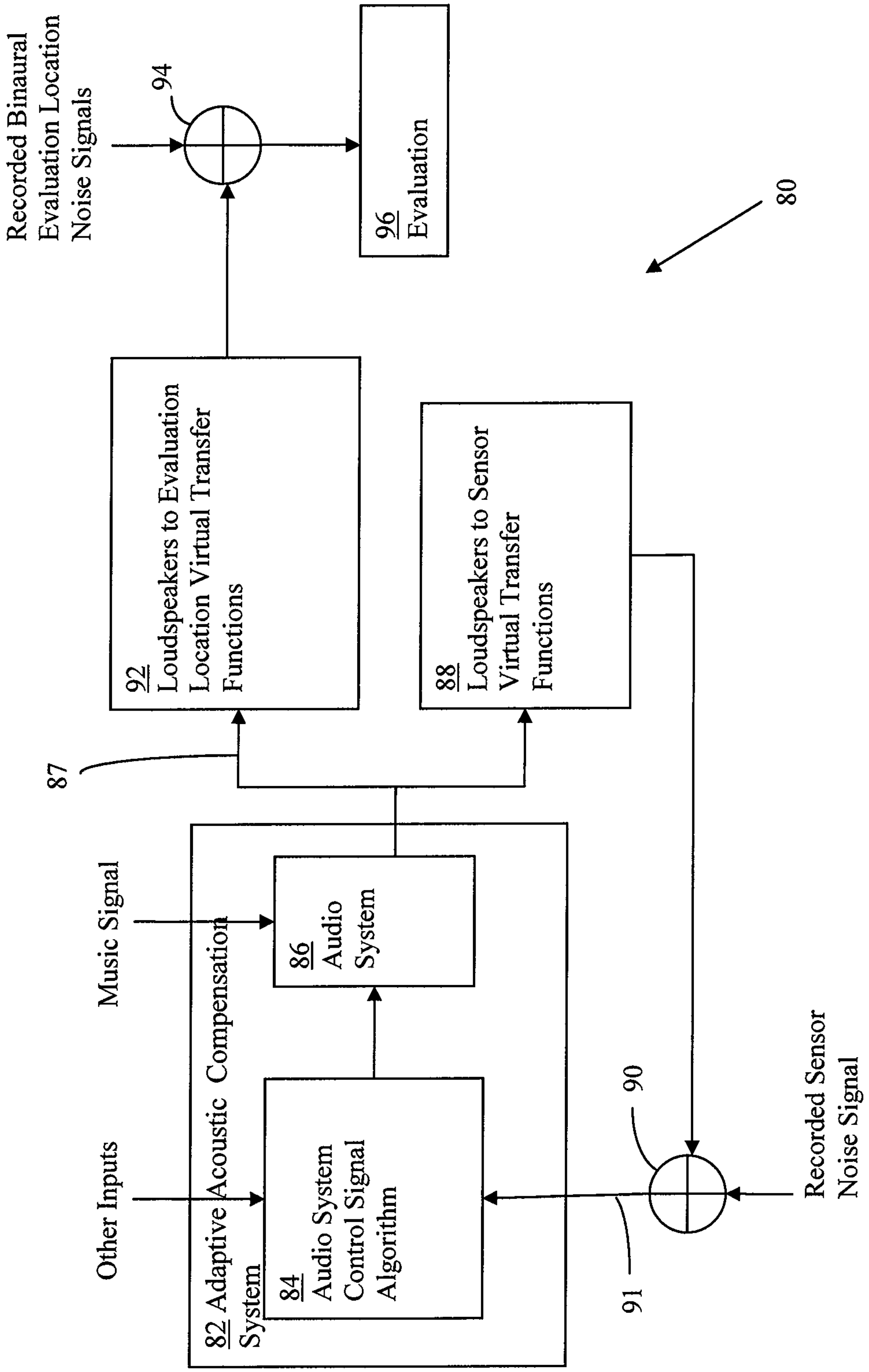
FIG. 3 is an alternative system for use in the simulated tuning of a dynamic audio system.

FIG. 3 discloses system 80 that is particularly adapted to allow for virtual tuning of vehicle cabin noise compensation systems. Adaptive acoustic compensation system 82 comprises audio system control signal algorithm 84 and audio system 86. Virtual sensor signal 91 comprises a combination 90 of audio signal 87 played through the loudspeakers to sensor virtual transfer functions 88, and the recorded sensor noise signal. Virtual sensor signal 91 is input to algorithm 84, which can be part of a signal processor that implements the vehicle noise cancellation processing. The output of algorithm 84 is provided to audio system 86, and controls the audio system playback parameters as necessary such that the simulated system changes made by the vehicle noise compensation system 80 are analogous to what would be experienced in the actual vehicle cabin.

In one non-limiting example, numerous recordings are made ahead of time in the vehicle cabin under various vehicle operating conditions such as different road surfaces, different vehicle speeds, different engine RPM values, different window states and the like, in accordance with system 10, FIG. 1. A test suite or database can then be created as described above. The database includes the noise recordings. The database may also include the conditions at the time of the recordings, and associated with the respective recordings. The test suite can be part of adaptive system 82. System 80 can then be used by a tuning engineer, for subjective tuning. System 80 can alternatively be used more automatically, i.e., for objective tuning. The particular vehicle operating conditions that are to be tested can be selected, and the corresponding sensor and binaural evaluation location noise signals retrieved from the database. These recorded noise signals are then input to combiners 90 and 94, respectively. Audio signal 87 is played through the loudspeakers to evaluation location virtual transfer functions 92 and provided to summer 94.

It is not necessary to capture information about road surfaces, speeds, and other test conditions. As long as the recording has taken place over all of the operating states that are of interest, virtual tuning can be accomplished. However, knowing where in the recording a particular condition occurs (a window is opened, for example), can be quite helpful. If, for example, the window open caused air flow noise in the microphone that caused the microphone signal to fluctuate wildly, the adaptive system behavior under this condition would likely not be correct. If the noise recording also indicates that the window opened when this behavior was observed, it would help in troubleshooting system behavior.

The simulated tuning innovation can simplify and speed up audio system tuning at a lower cost than manual tuning as it is currently performed. Simulated tuning as described herein is not subject to the availability of the listening environment (e.g., the target vehicle and the dynamometer and/or test track), as well as other equipment and support staff. Further, the innovation allows for off-site tuning, and provides the ability to rapidly switch between different vehicle operating states, neither of which are possible with the physical vehicle. These factors can save significant time and money in the audio system tuning effort. Further, the innovation leads to greater consistency because the simulated performance runs on a single set of baseline noise measurements, so the noise is exactly the same for each tuning run of the audio system. The innovation also allows for easy and quick comparison between various audio system control signal algorithms in the development of a noise compensation system, an EHC or EHE system, or other sound systems that use an adaptive audio processing system or a non-adaptive audio processing system. The innovation allows for easy and rapid comparison between system performance in various listening locations, avoiding the need to physically move between locations.

The innovation can be used for acoustic compensation systems that are adapted to be used for listening environments other than vehicle cabins; in this case the inputs to the acoustic compensation system can comprise operating conditions of the particular listening environment that affect sound heard at the evaluation locations.

While the innovation has been described as using a single set of virtual transfer functions associated with each evaluation location, in some embodiments a family of transfer functions may be obtained, where members of the family for one evaluation location are associated with different states of the physical system. For example, in order to virtually tune dynamic operation of an audio system for a convertible automobile, it may be necessary to obtain separate sets of transfer functions representing a first vehicle state where the vehicle top is up and a second vehicle state where the vehicle top is down. Similarly, different transfer functions representing other states such as the condition of various windows may be obtained.

A number of embodiments and options have been described herein. Modifications may be made without departing from the spirit and scope of the innovation. Accordingly, other embodiments are within the scope of the claims.

What is claimed is:

1. A method of virtually tuning an audio system that incorporates an acoustic compensation system, where the audio system is adapted to play audio signals in a listening environment using one or more sound transducers, the acoustic compensation system comprising an audio sensor located at a sensor location in the listening environment, wherein transfer functions from each sound transducer to the audio sensor location are inherent, and wherein there are a pair of sound evaluation locations in the listening environment at the approximate location of where the ears of a listener would be, where the sound evaluation locations are different than the sensor location, the method comprising:

recording noise at the sensor location;

recording noise at both of the sound evaluation locations simultaneously with recording noise at the sensor location;

creating virtual transfer functions for each sound transducer to the sensor location, based on the inherent transfer functions from each sound transducer to the sensor location;

processing audio signals through the virtual sound transducer to sensor location transfer functions; and creating a virtual sensor signal by combining the audio signals processed through the virtual sound transducer to sensor location transfer functions with the noise recorded at the sensor location.

2. The method of claim 1 wherein the sensor is either a microphone or an accelerometer.

3. A method of virtually tuning an audio system that incorporates an acoustic compensation system, where the audio system is adapted to play audio signals in a listening environment using one or more sound transducers, the acoustic compensation system comprising an audio sensor located at a sensor location in the listening environment, wherein transfer functions from each sound transducer to the audio sensor location are inherent, and wherein there is a sound evaluation location in the listening environment, and wherein transfer functions from each sound transducer to the evaluation location are inherent, the method further comprising:

recording noise at the sensor location;

recording noise at the sound evaluation location simultaneously with recording noise at the sensor location;

creating virtual transfer functions for each sound transducer to the sensor location, based on the inherent transfer functions from each sound transducer to the sensor location;

creating virtual transfer functions from each sound transducer to the evaluation location, based on the known transfer functions from each sound transducer to the evaluation location;

processing audio signals through the virtual sound transducer to sensor location transfer functions;

processing audio signals through the virtual sound transducer to evaluation location transfer functions;

creating a virtual sensor signal by combining the audio signals processed through the virtual sound transducer to sensor location transfer functions with the noise recorded at the sensor location; and creating an audio evaluation signal by combining the audio signals processed through the virtual sound transducer to evaluation location transfer functions with the noise recorded at the sound evaluation location.

4. The method of claim 3 wherein there is a pair of sound evaluation locations in the listening environment at the approximate locations where the ears of a listener would be, wherein noise is recorded simultaneously at both sound evaluation locations, wherein virtual transfer functions are created from each sound transducer to both sound evaluation locations, and wherein the audio evaluation signal is binaural.

5. The method of claim 4 wherein the acoustic compensation system further comprises a processor that processes the audio signals.

6. The method of claim 5 further comprising inputting the virtual sensor signal to the processor, wherein the virtual sensor signal is used by the processor to cause modifications to the audio signals.

7. The method of claim 6 further comprising inputting to the processor one or more acoustic compensation system inputs selected from the group of acoustic compensation system inputs consisting of an engine RPM signal, a music signal, a signal representative of vehicle speed, and a signal representative of the state of a vehicle function.

8. The method of claim 7 wherein one or more of the acoustic compensation system inputs are used by the processor to cause modifications to the audio signals.

9. The method of claim 5 further comprising recording one or more non-acoustic signals simultaneously with recording noise at the sensor and sound evaluation locations.

10. The method of claim 9 wherein the non-acoustic signals are selected from the group of signals consisting of an engine RPM signal, a signal indicative of throttle position, and a signal indicative of engine torque.

11. The method of claim 9 wherein the non-acoustic signals are recorded at multiple different locations.

12. The method of claim 9 further comprising inputting a recorded non-acoustic signal to the processor, wherein the non-acoustic signal is used by the processor to cause modifications to the audio signals.

13. The method of claim 12 wherein there are multiple evaluation locations in the listening environment, and wherein noise is recorded simultaneously at all of the sensor locations and all of the evaluation locations.

14. The method of claim 4 further comprising analyzing the audio evaluation signal.

15. The method of claim 14 wherein analyzing the audio evaluation signal comprises applying the audio evaluation signal to headphones.

16. The method of claim 3 wherein the recorded noise comprises sound in the listening environment, and the sound is recorded under varied environmental conditions of the listening environment.

17. The method of claim 16 further comprising associating in a database the recorded sound with the particular environmental conditions at the times of the recordings.

18. The method of claim 17 further comprising querying the database with particular environmental conditions, to retrieve the sound recorded under such conditions.

19. The method of claim 18 further comprising creating the virtual sensor signal and the audio evaluation signal using the retrieved sound.

20. A method of virtually tuning an audio system that includes an acoustic compensation system, where the audio system is adapted to play audio signals in a vehicle cabin over one or more sound transducers, the acoustic compensation system comprising an adaptive processor that processes the audio signals, and a microphone located at a sensor location in the vehicle cabin, wherein there is a sound evaluation location in the vehicle cabin, wherein transfer functions from each sound transducer to the sensor location are inherent, and wherein transfer functions from each sound transducer to the evaluation location are inherent, the method comprising:

recording sound at the sensor location, and binaurally recording sound at the sound evaluation location simultaneously with recording sound at the sensor location, wherein the sound is recorded with the vehicle operating under a variety of vehicle operating conditions;

creating virtual transfer functions from each sound transducer to the sensor location, based on the inherent transfer functions from each sound transducer to the sensor location;

creating virtual transfer functions from each sound transducer to the evaluation location, based on the inherent transfer functions from each sound transducer to the evaluation location;

processing audio signals through the virtual sound transducer to sensor location transfer functions;

processing audio signals through the virtual sound transducer to evaluation location transfer functions;

creating a virtual sensor signal by combining the audio signals processed through the virtual sound transducer to sensor location transfer functions with the sound recorded at the sensor location;

creating an audio evaluation signal by combining the audio signals processed through the virtual sound transducer to evaluation location transfer functions with the sound recorded at the sound evaluation location;

inputting the virtual sensor signal to the adaptive processor, wherein the virtual sensor signal is used by the adaptive processor to cause modifications to the audio signals;

inputting to the adaptive processor one or more acoustic compensation system inputs selected from the group of acoustic compensation system inputs consisting of an engine RPM signal, a music signal, a signal representative of vehicle speed, and a signal representative of the state of a vehicle function, wherein the acoustic compensation system inputs are used by the adaptive processor to cause modifications to the audio signals;

creating the virtual sensor signal and the audio evaluation signal using the recorded sound; and analyzing the audio evaluation signal, wherein analyzing the audio evaluation signal comprises applying the audio evaluation signal to headphones.

21. The method of claim 20 wherein the acoustic compensation system comprises multiple microphones located at multiple sensor locations in the vehicle cabin, and wherein there are multiple evaluation locations in the vehicle cabin, and wherein sound is recorded simultaneously at all of the sensor locations and binaurally at all of the evaluation locations.

22. A method of virtually tuning an audio system that includes an acoustic compensation system, where the audio system is adapted to create audio signals that modify or cancel engine harmonics in a vehicle cabin, the acoustic compensation system comprising a processor that processes the audio signals, and a microphone located at a sensor location in the vehicle cabin, wherein there is a sound evaluation location in the vehicle cabin, wherein transfer functions from each sound transducer to the sensor location are inherent, and wherein transfer functions from each sound transducer to the evaluation location are inherent, the method comprising:

recording sound at the sensor location, recording sound at the sound evaluation location, and recording one or more non-acoustic signals that are associated with the engine, all such recording taking place simultaneously, and wherein such recordings are made with the vehicle operating under a variety of engine operating conditions;

creating virtual transfer functions from each sound transducer to the sensor location, based on the inherent transfer functions from each sound transducer to the sensor location;

creating virtual transfer functions from each sound transducer to the evaluation location, based on the inherent transfer functions from each sound transducer to the evaluation location;

processing audio signals through the virtual sound transducer to sensor location transfer functions;

processing audio signals through the virtual sound transducer to evaluation location transfer functions;

creating a virtual sensor signal by combining the audio signals processed through the virtual sound transducer to sensor location transfer functions with the sound recorded at the sensor location;

creating an audio evaluation signal by combining the audio signals processed through the virtual sound transducer to evaluation location transfer functions with the sound recorded at the sound evaluation location;

inputting the virtual sensor signal and the recorded non-acoustic signals to the processor, wherein the inputs are used by the processor to cause modifications to the audio signals, to modify or cancel one or more engine harmonics;

inputting to the processor an engine RPM signal, wherein the engine RPM signal is used by the processor to cause modifications to the audio signals;

creating the virtual sensor signal and the audio evaluation signal using the recorded sound; and analyzing the audio evaluation signal.

23. The method of claim 22 wherein the audio system comprises multiple microphones located at multiple sensor locations in the vehicle cabin, and wherein there are multiple evaluation locations in the vehicle cabin, and wherein sound is recorded simultaneously at all of the sensor locations and at all of the evaluation locations.

24. A method of virtually tuning an audio system that includes an acoustic compensation system, where the audio system is adapted to play audio signals in a vehicle cabin over sound transducers, the audio signals used to modify engine harmonics in the vehicle cabin, wherein there is a sound evaluation location in the vehicle cabin, and wherein transfer functions from each sound transducer to the evaluation location are inherent, the method comprising:

recording sound at the sound evaluation location and simultaneously recording one or more non-acoustic signals that are associated with the engine, wherein such recordings are made with the vehicle operating under a variety of engine operating conditions;

determining engine harmonics from the recorded non-acoustic signals;

creating virtual transfer functions from each sound transducer to the evaluation location, based on the inherent transfer functions from each sound transducer to the evaluation location;

using the recorded non-acoustic signals to cause modifications to the audio signals, so as to modify one or more engine harmonics;

processing audio signals through the virtual sound transducer to evaluation location transfer functions;

creating an audio evaluation signal by combining the audio signals processed through the virtual sound transducer to evaluation location transfer functions with the sound recorded at the sound evaluation location; and analyzing the audio evaluation signal.

25. The method of claim 24 wherein analyzing the audio evaluation signal comprises applying the audio evaluation signal to headphones.

* * * * *